United States Patent [19]

Watanabe et al.

[11] Patent Number: 5,633,408
[45] Date of Patent: May 27, 1997

[54] PROCESS FOR PREPARING ALKANOLAMINES

[75] Inventors: Hiroyoshi Watanabe; Mutsuo Matsumura; Takashi Ohkawa; Kenji Suzuki, all of Osaka-fu, Japan

[73] Assignee: Mitsui Toatsu Chemicals, Inc., Tokyo, Japan

[21] Appl. No.: 493,804

[22] Filed: Jun. 22, 1995

[30] Foreign Application Priority Data

Jun. 28, 1994 [JP] Japan ................................ 6-146739
Jun. 28, 1994 [JP] Japan ................................ 6-146740
Jun. 28, 1994 [JP] Japan ................................ 6-146741

[51] Int. Cl.$^6$ .................................................. C07C 209/02
[52] U.S. Cl. ......................................... 564/475; 564/477
[58] Field of Search ................................... 564/477, 475

[56] References Cited

U.S. PATENT DOCUMENTS

| 2,186,392 | 1/1940 | Reynhart et al. | 260/584 |
| 3,849,262 | 11/1974 | Cocuzza | 203/38 |
| 4,119,670 | 10/1978 | Tsuchiya | 260/585 C |
| 4,169,856 | 10/1979 | Cocuzza et al. | 260/585 B |
| 4,438,281 | 3/1984 | Johnson, Jr. | 564/477 |
| 4,847,418 | 7/1989 | Gibson et al. | 564/477 |
| 5,334,763 | 8/1994 | Washington et al. | 564/475 |

FOREIGN PATENT DOCUMENTS

| 2645251 | 4/1978 | Germany . |
| 74047728 | 12/1974 | Japan . |
| 59013751 | 1/1984 | Japan . |
| 59033247 | 2/1984 | Japan . |
| 497093 | 12/1938 | United Kingdom . |
| WO93/21148 | 10/1993 | WIPO . |

OTHER PUBLICATIONS

Patent Abstracts of Japan, vol. 95, No. 004, May 31, 1995 & JP-A-07070006 (Mitsui Toatsu Chemicals, Inc.), Mar. 14, 1995 *Abstract*.

K. Weissermel and H. J. Arpe, "*Industrial Organic Chemistry—Main Materials and Intermediates*", (Japanese Edition together with a partial translation), Tokyo Kagaku Dojin, p. 149, 1978.

Zh. Prikl. Khim., vol. 56, "*Catalytic Reaction of Ethylene Oxide with Liquid Ammonia in the Presence of the Cation Exchanger Wofatite KPS*", pp. 1966–1971, 1983.

Primary Examiner—Brian M. Burn
Attorney, Agent, or Firm—Burns, Doane, Swecker & Mathis

[57] ABSTRACT

A process for preparing alkanolamines which comprises steps of reacting ammonia with an alkylene oxide in the presence of a carbonate of ammonia to obtain a crude alkanolamine solution, distilling off ammonia, carbon dioxide and water to regulate the content of carbon dioxide in the crude alkanolamine solution to 1% by weight or less, and distilling the crude alkanolamine solution to separate and collect the alkanolamines, whereby the production ratio of a monoalkanolamine can be increased and impurities can be decreased.

21 Claims, No Drawings

PROCESS FOR PREPARING ALKANOLAMINES

BACKGROUND OF THE INVENTION

1. Field of the Invention

The present invention relates to a process for preparing alkanolamines such as ethanolamines and isopropanolamines. More specifically, it relates to a process for particularly and selectively preparing monoalkanolamines.

2. Description of the Related Art

Alkanolamines can easily be obtained by reacting an alkylene oxide with aqueous ammonia, and also in an industrial scale, they have been manufactured by this process.

However, the alkanolamines obtained by the above-mentioned process are present in the state of a mixture of a monoalkanolamine, a dialkanolamine and a trialkanolamine, and it is an important theme to control the production ratio of these components. Particularly in recent years, the demand for the monoalkanolamine is larger as compared with that of the dialkanolamine and the trialkanolamine, and a technique for preparing the monoalkanolamine in a high production ratio has been required.

In general, with regard to a method for manufacturing the monoalkanolamine in a high production ratio by, for example, the reaction of ethylene oxide and ammonia, the following matters are known. That is to say, the reactivity between ethylene oxide and ammonia is lower as compared with the reactivity between ethylene oxide and monoethanolamine or diethanolamine, and therefore the ratio of the reaction products depends upon the ratio of ammonia to ethylene oxide. Thus, as ammonia is used in large excess, the production ratio of the monoethanolamine increases (K. Weissermel and H. J. Arpe, Translation supervised by Mitsuaki Mukouyama, "Industrial Organic Chemistry—Main Materials and Intermediates—", Tokyo Kagaku Dojin, p. 149 (1978).

However, if aqueous ammonia is used and a molar ratio of ammonia/the alkylene oxide is high, the production ratio of the monoalkanolamine can be increased, but the volumetric efficiency of a reactor deteriorates, and excess aqueous ammonia is required to be collected and recycled. In consequence, the energy unit requirement decreases and the load of the ammonia collection system and the water collection system increases inconveniently.

In order to solve such problems, there is a method in which the water content of the aqueous ammonia is minimized, but since the reaction of the alkylene oxide and ammonia proceeds by virtue of the function of water as a catalyst, such a method causes the deterioration of activity. Thus, as some measures to the above-mentioned inconvenience, there have been suggested a method of using a solid acid catalyst and increasing the reaction temperature (e.g., Japanese Patent Application Laid-open No. 47728/1974; Zh. Prikl. Khim., Vol. 56, p. 1966 (1983); and U.S. Pat. No. 4,438,281) and another method in which the reaction is carried out in a supercritical state (Japanese Patent Application Laid-open Nos. 13751/1984 and 33247/1984), but these methods have a problem that reaction pressure is high and so a high-pressure reactor is required, and another problem that the load of the ammonia collection system increases.

On the other hand, there are known methods in which when ammonia reacts with an alkylene oxide to prepare alkanolamines, a carbonate of ammonia is used, whereby the production ratio of the monoalkanolamine can be increased under relatively gentle conditions (British Patent No. 497,093 and U.S. Pat. No. 2,186,392).

The present inventors have intensively investigated a process in which ammonia reacts with an alkylene oxide in the presence of a carbonate of ammonia in accordance with the above-mentioned U.S. Pat. No. 2,186,392 to prepare the alkanolamines, and it has been confirmed that even if ammonia is not used in large excess relative to the alkylene oxide, the production ratio of the monoalkanolamine can be remarkably increased.

Next, it was tried to separate, from a reaction solution, the monoalkanolamine, the dialkanolamine and the trialkanolamine which were products. That is to say, after ammonia, most of the carbon dioxide and water had been distilled off, the alkanolamines which were the products were separated from the resultant bottoms, and at this time, there was elucidated a problem, which was heretofore unknown, which impurities such as nitrogen-containing compounds such as carbamic acid and carbamic acid esters and nitrogen-containing heterocyclic compounds such as oxazolidone and N-hydroxyethylpiperazine were present in the alkanolamines.

SUMMARY OF THE INVENTION

An object of the present invention is to provide a process for preparing alkanolamines in which the content of the above-mentioned impurities is decreased in separating the alkanolamines from a reaction solution obtained by reacting ammonia with an alkylene oxide in the presence of a carbonate of ammonia.

The present inventors have investigated to solve the above-mentioned problems. As a result, the present invention has now been attained.

That is to say, the present invention is connected with the following three aspects.

(1) A process for preparing alkanolamines which comprises
  a step of reacting ammonia with an alkylene oxide in the presence of a carbonate of ammonia to obtain a crude alkanolamine solution,
  a step of distilling off ammonia, carbon dioxide and water to regulate the content of carbon dioxide in the crude alkanolamine solution to 1% by weight or less, and
  a step of distilling the crude alkanolamine solution to separate and collect the alkanolamines.

(2) A process for preparing alkanolamines which comprises
  a step of reacting ammonia with an alkylene oxide in the presence of a carbonate of ammonia to obtain a crude alkanolamine solution,
  a step of subjecting the obtained crude alkanolamine solution to a heat treatment in a range of from 160° to 220° C. in the presence of water, distilling off carbon dioxide at a temperature equal to or higher than the heat treatment temperature, and then distilling off water to regulate the content of carbon dioxide in the crude alkanolamine solution to 1% by weight or less, and
  a step of distilling the crude alkanolamine solution to separate and collect the alkanolamines.

(3) A process for preparing alkanolamines which comprises
  a step of reacting ammonia with an alkylene oxide in the presence of a carbonate of ammonia to obtain a crude alkanolamine solution, a step of reacting the obtained crude alkanolamine solution with a base in a range of from 140° to 200° C. in the presence of water, and then distilling off water to regulate the content of carbon dioxide in the crude alkanolamine solution to 1% by weight or less, and a step of distilling the crude alkanolamine solution to separate and collect a monoalkanolamine.

According to the present invention, the production ratio of a monoalkanolamine can be remarkably increased, and impurities such as nitrogen-containing compounds such as carbamic acid and carbamic acid esters and nitrogen-containing heterocyclic compounds such as oxazolidone and N-hydroxyethylpiperazine contained in the alkanolamines can be remarkably reduced. Accordingly, the present invention permits the manufacture of the high-quality alkanolamines in an economically and industrially extremely advantageous manner.

DETAILED DESCRIPTION OF THE PREFERRED EMBODIMENTS

According to the investigation by the present inventors, it is apparent that a carbonate used in the reaction of ammonia with an alkylene oxide is mainly present in the forms of carbamic acid, carbamic acid esters, carbonates and bicarbonates derived from alkanolamines, after the completion of the reaction. These carbon dioxide-containing substances are decomposed by heating a reaction solution to liberate carbon dioxide, and therefore it is possible to separate carbon dioxide from the reaction solution by distillation. However, the above-mentioned carbon dioxide-containing substances not only liberate carbon dioxide when heated but also successively react to change into nitrogen-containing heterocyclic compounds such as N-hydroxyethylpiperazine. This tendency is noticeable when the reaction solution is heated and distilled after ammonia, most of carbon dioxide and water have been distilled off from a crude alkanolamine solution obtained by reacting ammonia with the alkylene oxide in the presence of a carbonate of ammonia. Furthermore, it is apparent that since water is not present in the reaction solution, carbon dioxide and the alkanolamines present in the solution react with each other to noticeably produce compounds such as oxazolidone.

Next, the present inventors have intensively investigated with the intention of controlling the production of these impurities, and as a result, the present invention has been attained on the basis of the following discoveries.

(1) Impurities such as nitrogen-containing compounds such as carbamic acid and carbamic acid & esters and nitrogen-containing heterocyclic compounds such as oxazolidone and N-hydroxyethylpiperazine present in the alkanolamines can be remarkably reduced, if the concentration of carbon dioxide present in the crude alkanolamine solution is controlled to a certain level or less in heating and distilling the solution.

(2) These impurities can be remarkably reduced, if distillation is carried out at a certain column bottom temperature or less of a distillation column in heating and distilling the crude alkanolamine solution to obtain a monoalkanolamine.

(3) These impurities can be remarkably reduced, if heating and distillation are carried out, with a residence time in the distillation column being within a certain time, prior to heating and distilling the crude alkanolamine solution to separate and collect the monoalkanolamine.

Furthermore, the present inventors have intensively investigated a technique for lowering the concentration of carbon dioxide present in the crude alkanolamine solution. As a result, it is apparent that carbon dioxide-containing substances such as carbamic acid, carbamic acid esters, carbonates and bicarbonates derived from the alkanolamines liberate carbon dioxide when decomposed by heating a reaction solution, and therefore it is possible to separate carbon dioxide from the reaction solution by heating and distillation. However, it has been understood that this operation alone is insufficient to achieve the purpose of lowering, to a certain level or less, the concentration of carbon dioxide contained in the solution in heating and distilling the crude alkanolamine solution. The reason is that carbon dioxide used at the time of the reaction between ammonia and the alkylene oxide is also present as compounds such as oxazolidone after the completion of the reaction, and when the crude alkanolamine solution is heated and distilled to separate and collect the monoalkanolamine, these compounds are decomposed by heating to release carbon dioxide and on the other hand, for example, oxazolidone reacts with the monoalkanolamine to change into imidazolidone derivatives, which leads to the loss of the monoalkanolamine and the increase of the impurities. Therefore, in the present invention, it is required that compounds such as oxazolidone are decomposed prior to the step in which the crude alkanolamine solution is heated and distilled to separate and collect the monoalkanolamine. The present inventors have further investigated a technique for decomposing compounds such as oxazolidone, and as a result, the following methods have been found.

(4) A method which comprises reacting ammonia with an alkylene oxide in the presence of a carbonate of ammonia to obtain a crude alkanolamine solution, subjecting the crude alkanolamine solution to a heat treatment in a range of from 160° to 220° C. in the presence of water, heating and distilling the thus thermally treated solution at a temperature equal to or higher than the heat treatment temperature to remove carbon dioxide, further heating and distilling the solution to distill off water, and then separating and collecting a monoalkanolamine by heating and distillation.

(5) A method which comprises reacting ammonia with an alkylene oxide in the presence of a carbonate of ammonia to obtain a crude alkanolamine solution, reacting the thus obtained crude alkanolamine solution with a base in a range of from 140° to 200° C. in the presence of water, heating and distilling the solution to distill off water, and then separating and collecting a monoalkanolamine by heating and distillation.

According to these methods, the concentration of carbon dioxide in the crude alkanolamine solution can be lowered prior to the separation and collection of the monoalkanolamine.

Now, the present invention will be described in more detail.

The term of "alkanolamines" referred to in the present invention is a general term of amines including a monoalkanolamine, a dialkanolamine and a trialkanolamine. For example, in the case that ethylene oxide is used as a material, the alkanolamines mean monoethanolamine, diethanolamine and triethanolamine, and in the case that propylene oxide is used as the material, the alkanolamines mean monoisopropanolamine, diisopropanolamine and triisopropanolamine.

Furthermore, the concentration of carbon dioxide referred to in the present invention can be defined as follows. That is to say, the concentration of carbon dioxide which exists in the forms of carbamic acid, carbamic acid esters, carbonates, bicarbonates and the like derived from the alkanolamines can be determined by, for example, a gas chromatography analysis method. However, this method cannot analyze carbon dioxide contained in compounds such as oxazolidone. In the present invention, therefore, an aqueous barium hydroxide solution is added to a solution to be analyzed, and heating is then conducted at 170° C. for about 2 hours to decompose compounds such as oxazolidone. Afterward, the resultant barium carbonate precipitate is subjected to gravimetric determination. The thus determined concentration is defined as the concentration of carbon dioxide.

The alkanolamines referred to in the present invention mean alkanolamines obtained by reacting ammonia with an alkylene oxide in the presence of a carbonate of ammonia, and a preparation process of them will be described.

Examples of the carbonate of ammonia referred to herein include ammonium carbonate, ammonium bicarbonate and ammonium carbamate. In addition, a carbonate of ammonia which can be obtained by mixing aqueous ammonia with carbon dioxide in an optional ratio is also usable as the carbonate. Carbon dioxide which can be used in this case can be employed in any state of dry ice, liquid carbon dioxide, a carbonate liquid formed by dissolving carbon dioxide in water, and gaseous carbon dioxide. Moreover, the aqueous ammonia means either of conventional aqueous ammonia obtained by dissolving ammonia in water, or a mixture of water with liquid ammonia or gaseous ammonia.

The amount of the carbonate of ammonia to be used is in the range of from 0.01 to 10 moles, preferably from 0.02 to 8 moles in terms of carbonate ions per mole of the alkylene oxide. As the amount of the carbonate of ammonia to be used is increased, the monoalkanolamine can be selectively prepared, while the production the dialkanolamine and the trialkanolamine is inhibited.

Examples of the alkylene oxide which can be used in the process of the present invention include ethylene oxide, propylene oxide, epichlorohydrin, glycidol, 1,2-epoxybutane, trans-2,3-epoxybutane, isobutylene oxide, cyclohexene oxide and styrene oxide. Of these alkylene oxides, ethylene oxide and propylene oxide are preferable.

No particular restriction is put on the concentration of aqueous ammonia which is used in the process of the present invention, but the ammonia concentration is usually in the range of from 1 to 80% by weight, preferably from 5 to 60% by weight. The amount of ammonia to be used is decided as the total of the amount of ammonia contained in the used carbonate of ammonia and the amount of ammonia used as aqueous ammonia, but this total is in the range of from 1 to 10 moles, preferably from 2 to 8 moles per mole of the alkylene oxide. In the process of the present invention, water is used as a solvent, but any solvent can be used in the form of a mixed solvent with water or singly, as long as it does not have a bad influence on the reaction.

In the process of the present invention, temperature at which ammonia is reacted with the alkylene oxide in the presence of the carbonate of ammonia is in the range of from 10° to 150° C., preferably from 20° to 100° C. Pressure under which the reaction is carried out depends upon self-generated pressure at the predetermined reaction temperature, and the pressure can be attained by maintaining this pressure. Usually, it is in the range of from 1 to 50 kg/cm$^2$G. Reaction time depends upon the amount of the carbonate of ammonia, the amount of ammonia, the amount of the alkylene oxide, the concentration of aqueous ammonia, the reaction temperature and the like, but it is usually in the range of from 5 minutes to 10 hours, preferably from 10 minutes to 5 hours. The process of the present invention can be carried out any one of a batch method, a semi-batch method and a continuous method.

In the process of the present invention, the thus obtained reaction solution which is rich in the monoalkanolamine is heated and distilled to separate ammonia, most of the carbon dioxide and water.

In the process of the present invention, it is very important to heat and distill the crude alkanolamine solution in which the content of carbon dioxide is controlled, prior to heating and distilling the crude alkanolamine solution to separate the monoalkanolamine. In this case, the content of carbon dioxide is usually 1% by weight or less with respect to the weight of the crude alkanolamine solution.

For the purpose of heating and distilling the reaction solution to separate ammonia, most of the carbon dioxide and water therefrom, some methods are practical, and methods by which the content of carbon dioxide in the crude alkanolamine solution can be regulated to 1% by weight or less with respect to the weight of the crude alkanolamine solution are all acceptable in the present invention.

The procedure of these operations will be described in detail. The reaction solution is first heated and distilled to distill off ammonia, and carbon dioxide which exists mainly in the forms of carbon dioxide-containing compounds such as carbamic acid, carbamic acid esters, carbonates and bicarbonates derived from the alkanolamines are thermally decomposed and then separated through a column top. It is very important to carry out the heating and distillation at a distillation column bottom temperature of 100° C. or more, and preferably the heating and distillation are done at a distillation column bottom temperature of 100° to 200° C., whereby the concentration of carbon dioxide in the resultant bottoms containing the alkanolamines and water can be noticeably decreased. If the distillation temperature is less than 100° C., the thermal decomposition efficiency into carbon dioxide is very poor, and if it is more than 200° C., the distillation pressure increases, so that the cost of facilities increases uneconomically. The distillation pressure depends upon the composition of the alkanolamines and water in a column bottom solution, but the pressure should be decided so that the column bottom temperature may be maintained at 100° C. or more. In the case of ethanolamine among the alkanolamines, the distillation pressure is usually 500 torr or more. The residence time of the reaction mixture in the distillation column is 2 hours or less, preferably 1 hour or less. The heating and distillation may be carried out by a batch system or a continuous system, but the continuous system is preferable. The distillation can be carried out by simple distillation in which a conventional distillation operation is used, but in general, it is preferably carried out by rectification in which a packed tower, a bubble cap tower or a stepped tower comprising porous plates or the like is used. In this case, the number of theoretical plates in the distillation column is in the range of from 1 to 20 plates, preferably from 5 to 15 plates in each of a concentrating section and a collecting section. Furthermore, a reflux ratio is in the range of from 0 to 3, preferably from 0.1 to 2.0.

In the present invention, the bottoms from which ammonia and a part of carbon dioxide have been distilled off by the thermal decomposition are delivered to a step in which water is separated, and the bottoms are further thermally treated to further remove carbon dioxide. That is to say, the bottoms are heated and distilled to remove water and carbon dioxide which exists mainly in the forms of carbon dioxide-containing compounds such as carbamic acid, carbamic acid esters, carbonates and bicarbonates derived from the alkanolamines, in which carbon dioxide are generated by thermally decomposing the carbon dioxide-containing compounds and then separated through a column top. It is very important to carry out the heating and distillation at a distillation column bottom temperature of 140° to 220° C., and preferably the heating and distillation are done at a distillation column bottom temperature of 150 to 210° C., whereby the concentration of carbon dioxide in the resultant bottoms containing the crude alkanolamine solution can be noticeably lowered. If the distillation temperature is lower than 140° C., the thermal decomposition efficiency into carbon dioxide is very poor, and if it is higher than 220° C., the alkanolamines thermally change unpreferably. The distillation pressure depends upon the composition of the alkanolamines in the column bottom solution, but the pressure should be decided so that the column bottom temperature may be maintained at 140° C. or higher. The residence time of the reaction mixture in the distillation column is 2 hours or less, preferably 1 hour or less. The heating and distillation may be carried out by a batch system or a continuous system, but the continuous system is preferable. The distillation can be carried out by simple distillation in which a conventional distillation operation is used, but in general, it is preferably carried out by rectification in which a packed tower, a bubble cap tower or a stepped tower comprising porous plates or the like is used. In this case, the number of theoretical plates in the distillation column is in the range of from 1 to 20 plates, preferably from 5 to 15 plates in each of a concentrating section and a collecting section. Furthermore, a reflux ratio is in the range of from 0 to 3, preferably from 0.1 to 2.0.

In the present invention, a heat treatment is carried out prior to a step in which water is separated, whereby compounds such as oxazolidone can be decomposed to further lower the concentration of carbon dioxide in the crude alkanolamine solution. This is due to the hydrolysis of compounds such as oxazolidone in the presence of water by heating. Therefore, the reaction solution may be thermally treated as is, but it is preferable that the reaction solution is previously treated to remove ammonia by heating and distilling in a distillation column, as well as carbon dioxide which exists mainly in the forms of carbon dioxide-containing compounds such as carbamic acid, carbamic acid esters, carbonates and bicarbonates derived from the alkanolamines by thermal decomposition of the carbon dioxide-containing compounds in the column, and the thus treated solution obtained from the bottom of the column is then subjected to the former heat treatment. The temperature of the heat treatment is in the range of from 160° to 220° C., preferably from 170° to 210° C. If the temperature is lower than 160° C., the hydrolysis efficiency is poor, and if it is higher than 220° C., the quality change of the alkanolamines occurs unpreferably. The time of the heat treatment is in the range of from 0.1 to 4 hours, preferably from 0.5 to 3 hours. The heat treatment may be carried out by a batch system or a continuous system. Carbon dioxide generated by the heat treatment is next separated by the heating and distillation. In this carbon dioxide separation step, the heating and distillation are carried out at a temperature equal to or higher than the heat treatment temperature. Distillation pressure depends upon the composition of the alkanolamines in a column bottom solution, but the pressure should be decided so that the column bottom temperature may be maintained at distillation temperature or more. The residence time of the reaction mixture in the distillation column is 2 hours or less, preferably 1 hour or less. The heating and distillation may be carried out by a batch system or a continuous system, but the continuous system is preferable. The distillation can be carried out by simple distillation in which a conventional distillation operation is used, but in general, it is preferably carried out by rectification in which a packed tower, a bubble cap tower or a stepped tower comprising porous plates or the like is used. In this case, the number of theoretical plates in the distillation column is in the range of from 1 to 10 plates, preferably from 2 to 5 plates in each of a concentrating section and a collecting section. Furthermore, the reflux ratio is in the range of from 0 to 1.

In this carbon dioxide separation step, the heating and distillation may be replaced with the introduction of steam having a temperature equal to or higher than the heat treatment temperature through a column bottom to accomplish steam stripping, thereby separating carbon dioxide.

In addition, as another embodiment of the present invention, the heat treatment can be carried out, while carbon dioxide liberated simultaneously with the heat treatment is removed from the system.

The column bottom solution from which carbon dioxide has been thus separated is then delivered to a step where water is removed by distillation.

In the present invention, on the upstream side of the step for removing water, there may be effectively disposed a step where the column bottom solution reacts with a base so that compounds such as oxazolidone may be decomposed to further lower the concentration of carbon dioxide in the crude alkanolamine solution. According to this step, compounds such as oxazolidone are hydrolyzed in the presence of the base by heating to liberate carbon dioxide formed as a salt of the base, and this hydrolyzation is, needless to say, carried out in the presence of water. Therefore, the reaction solution may react with the base, but it is preferable that the reaction solution is previously subjected to remove ammonia by heating and distilling in a distillation column, as well as carbon dioxide which exists mainly in the forms of carbon dioxide-containing compounds such as carbamic acid, carbamic acid esters, carbonates and bicarbonates derived from the alkanolamines by thermal decomposition of the carbon dioxide-containing compounds in the column, and the thus treated bottoms then react with the base.

Typical examples of the usable base include hydroxides of alkali metals and alkaline earth metals.

Reaction temperature is in the range of from 140° to 200° C., preferably 150° to 190° C. If the reaction temperature is lower than 140° C., the hydrolysis efficiency is poor, and if it is higher than 220° C., the quality change of the alkanolamines occurs unpreferably. Heat treatment time is in the range of from 0.1 to 4 hours, preferably from 0.5 to 3 hours. The heat treatment may be carried out by a batch system or a continuous system.

The selected base reacts with liberated carbon dioxide to become a carbonate. For example, in the case that barium hydroxide is used as the base, the precipitate of barium carbonate is deposited, and in the case that calcium hydroxide is used, the precipitate of calcium carbonate is deposited. Particularly in the case of calcium hydroxide, since calcium hydroxide itself does not dissolve in the aqueous alkanolamine solution, it is preferably separated by filtration or centrifugal separation, after the completion of the reaction. The base is used in a minimum amount necessary to produce the salt with carbon dioxide present in the system. This amount can be beforehand decided by analyzing carbon dioxide by the use of barium hydroxide. Next, the column bottom solution from which carbon dioxide has been thus separated is delivered to a step where water is removed by distillation.

In the present invention, it is very important to heat and distill the crude alkanolamine solution in which the content of carbon dioxide is controlled, prior to heating and distilling the crude alkanolamine solution to separate the monoalkanolamine. The content of carbon dioxide is usually 1% by weight or less, preferably 0.8% by weight or less, more preferably 0.7% by weight or less with respect to the weight of the crude alkanolamine solution. If the crude alkanolamine solution containing carbon dioxide in an amount not more than in this range is distilled, impurities such as nitrogen-containing compounds such as carbamic acid and carbamic acid esters and nitrogen-containing heterocyclic compounds such as oxazolidone and N-hydroxyethylpiperazine can be remarkably decreased. On the other hand, if the crude alkanolamine solution containing carbon dioxide in an amount more than in this range is distilled, said impurities remarkably increase, with the result that the purity of the alkanolamines deteriorates.

According to distillation conditions in the process of the present invention under which the reaction solution is heated and distilled to separate ammonia, most of the carbon dioxide and water, the content of carbon dioxide in the crude alkanolamine solution can be controlled so as to be within the desired range of the present invention. However, if the content of carbon dioxide in the crude alkanolamine solution is not within the range of the present invention, alkanolamines such as the monoalkanmolamine may be added to the crude alkanolamine solution so that the content of carbon dioxide may be within the range of the present invention.

The distillation and separation of the monoalkanmolamine from the crude alkanolamine are carried out by distilling the crude alkanolamine so that the column bottom temperature of the distillation column may be maintained usually at 200° C. or lower, preferably 180° C. or lower. Distillation pressure depends upon the composition of the ethanolamines and the like, but the pressure should be such as to maintain the column bottom temperature at 200° C. or lower, preferably 180° C. or lower. Usually, the pressure is 760 torr or less. The residence time of the reaction mixture in the distillation column is 3 hours or less, preferably 2 hours or less. If the residence time is longer than the above-mentioned time, the alkanolamines thermally change unpreferably. The heating and distillation may be carried out by a batch system or a continuous system. In this case, in order to inhibit carbon dioxide from getting into monoethanolamine which is a product, for example, a procedure is effective which comprises separating and collecting monoethanolamine having a low carbon dioxide content through a column top, drawing monoethanolamine containing carbon dioxide by side cut, and then recycling the thus drawn monoethanolamine containing carbon dioxide to before the step in which ammonia, carbon dioxide and water are distilled off. Furthermore, another embodiment is also effective which comprises first drawing monoethanolamine containing carbon dioxide through the column top, heating and distilling the drawn solution to separate and collect monoethanolamine having a low carbon dioxide content through the column top, drawing monoethanolamine containing carbon dioxide through a column bottom, and recycling the monoethanolamine containing carbon dioxide to before the step in which ammonia, carbon dioxide and water are distilled off. The distillation can be carried out by simple distillation in which a conventional distillation operation is used, but in general, it is preferably carried out by rectification in which a packed tower, a bubble cap tower or a stepped tower comprising porous plates or the like is used. In this case, the number of theoretical plates in the distillation column is in the range of from 1 to 20 plates, preferably from 5 to 15 plates in each of a concentrating section and a collecting section. Furthermore, the reflux ratio is in the range of from 0 to 3, preferably from 0.1 to 2.0.

When ethanolamine is picked up as the alkanolamine, bottoms from which monoethanolamine has been separated by heating and distilling the crude alkanolamine are further heated and distilled to separate impurities mainly comprising ethylene glycol, diglycolamine and the like which are intermediate fractions of monoethanolamine and diethanolamine, and diethanolamine and triethanolamine are then separated by conventional techniques, respectively.

Now, the present invention will be described in more detail with reference to examples.

Incidentally, the analysis of carbon dioxide was carried out by both of a gas chromatography method (hereinafter referred to as "GC method") (filler=Polapack® Q, detector= TCD) and a gravimetric analysis method (hereinafter referred to as "gravimetric analysis method") which comprised adding an aqueous barium hydroxide solution to a sample, heating it at 170° C. for about 2 hours, and then carrying out the gravimetric determination of the precipitate of the resultant barium carbonate.

EXAMPLE 1

[Reaction Step]

A liquid mixture comprising 302.4 g of a 35% aqueous ammonium carbonate solution and 133.1 g of 39% aqueous ammonia was fed to a stainless steel reactor (internal volume=250 ml) having an inner diameter of 6 mm and a total length of 9 m through its inlet at 435.5 g/hr by a pump, and ethylene oxide (hereinafter abbreviated to "EO") was simultaneously fed thereto at 65.9 g/hr by a pump. The reactor was maintained at 40° C. by a thermostatic chamber, and pressure was set to 7 kg/cm$^2$G. The above conditions corresponded to an ammonia/EO molar ratio of 3.51 and a carbonate ion/EO molar ratio of 0.73. Reaction was continuously carried out for 5 hours, and after the system had become a steady state, a solution at the outlet of the reactor was analyzed. The results are shown as follows (hereinafter monoethanolamine was abbreviated to MEA, diethanolamine was abbreviated to DEA, and triethanolamine was abbreviated to TEA).

Flow rate of solution: 501.4 g/hr
Composition: Ammonia=13.5 wt. %, carbon dioxide=9.7 wt. %, water=59.1 wt. %, MEA=13.1 wt. %, DEA=2.9 wt. %, TEA=1.7 wt. %, ethylene glycol (hereinafter abbreviated to "EG")=1300 ppm, and oxazolidone (hereinafter abbreviated to "OXA")=240 ppm.

It is apparent from the above-mentioned results that the conversion of EO was 100%, MEA, DEA and TEA were produced at 65.7 g/hr, 14.5 g/hr and 8.5 g/hr, respectively, and the production ratio of MEA, DEA and TEA was 74.0:16.4:9.6.

[Separation Step of Ammonia and Carbon Dioxide]

Next, ammonia and carbon dioxide were collected from a reaction solution synthesized in the reaction step. That is to say, a gas collection column was a packed tower (the number of theoretical plates=5 plates in a concentrating section and 5 plates in a collecting section) having an inner diameter of 40 mm and a height of 80 cm, and any reflux was not carried out. To this collection column, the reaction solution was fed at 1 kg/hr and the column bottom was heated up to 158° C. on an oil bath, and distillation was then carried out, with the column bottom residence time being 1 hour. In this case, the pressure in the column was 3.5 kg/cm$^2$. The results of the reaction after the system had reached a steady state were as follows.

Gas Collection Column Bottom

Flow rate of solution: 450 g/hr

Composition: Water=41.0 wt. %, MEA=41.4 wt. %, DEA=9.8 wt. %, TEA=5.8 wt. %, EG=7750 ppm, OXA=673 ppm, carbon dioxide=2691 ppm (a GC method) and 5223 ppm (a gravimetric method)

[Separation Step of Water and Carbon Dioxide]

Next, water and carbon dioxide were separated from a column bottom solution in the gas collection column. That is to say, the column bottom solution in the gas collection column was fed at a rate of 500 g/hr to a flask of a distillation device equipped with the flask having a column bottom volume of 1000 ml, a packed tower (the number of theoretical plates=10 plates in a concentrating section and 5 plates in a collecting section) having an inner diameter of 26 mm and a height of 270 cm and a reflux condenser. At this time, a pressure of 233 torr was applied and the column bottom solution was heated up to 148° C., and while the reflux ratio was maintained at 0.5, distillation was continuously carried out for 4 hours, with the column bottom residence time being 1 hour.

The results of the reaction after the system had reached a steady state were as follows.

Column Bottom

Flow rate of drawn solution: 295 g/hr

Composition: Water=0.26 wt. %, MEA=72.7 wt. %, DEA=17.1 wt. %, TEA=9.1 wt. %, EG=1.5 wt. %, OXA=966 ppm, carbon dioxide=160 ppm (a GC method) and 6140 ppm (a gravimetric method)

[Separation Step of MEA]

Next, MEA was collected from the column bottom solution from which water and carbon dioxide had been separated. That is to say, there was used a device equipped with a flask having a column bottom volume of 300 ml and a column having an inner diameter of 26 mm and a height of 270 cm, the intermediate portion of the column being provided with a feed section for a distillation material solution, the intermediate portion between a column top and the feed section for the material solution being provided with a side cut portion. As a distillation column, there was used a packed tower in which the number of theoretical plates was 5 plates between a column bottom portion and the solution feed portion and 10 plates between the side cut portion and the column top. To this distillation device, the column bottom solution from which water and carbon dioxide had been separated was fed at a rate of 500 g/hr. At this time, a pressure of 10 torr was applied and the column bottom solution was heated up to 175° C., and distillation was continuously carried out for 4 hours, with the column bottom residence time being 1.8 hours. In this case, the reflux ratio was maintained at 0.5 and a ratio of the amount of the solution distilled out through the column top to the amount of the solution drawn by side cut was maintained at 0.2.

The results of the reaction after the system had reached a steady state were as follows.

Column Top

Flow rate of distilled solution: 303 g/hr

Composition: In addition to MEA and a trace amount of carbon dioxide, 5 ppm of unknown components was observed.

Column Side

Flow rate of distilled solution: 60 g/hr

Composition: In addition to MEA, 4.2 wt. % of carbon dioxide was observed.

Column Bottom

Flow rate of drawn solution: 137 g/hr

Composition: In addition to DEA and TEA, there were observed 200 ppm of hydroxyethyl carbamate, 6515 ppm of oxazolidone and 1500 ppm of nitrogen-containing heterocyclic compounds such as N-hydroxyethylpiperazine.

COMPARATIVE EXAMPLE 1

Distillation was continuously carried out for 4 hours by the same procedure as in an MEA collection experiment of Example 1 except that with regard to distillation conditions, pressure was changed to 80 torr and column bottom temperature was changed to 220° C.

The results of reaction after the system had reached a steady state were as follows.

Column Top

Flow rate of distilled solution: 303 g/hr

Composition: In addition to MEA and a trace amount of carbon dioxide, 85 ppm of unknown components was observed.

Column Bottom

Flow rate of drawn solution: 137 g/hr

Composition: In addition to DEA and TEA, there were observed 621 ppm of hydroxyethyl carbamate, 1.3 wt. % of oxazolidone and 5100 ppm of nitrogen-containing heterocyclic compounds such as N-hydroxyethylpiperazine.

EXAMPLE 2

The collection experiment of MEA was made by the same procedure as in Example 1 except that there was used a crude ethanolamine solution having a carbon dioxide concentration of 1000 ppm (the GC method, 7000 ppm measured by the gravimetric method) obtained by adding dry ice to a column bottom solution from which water and carbon dioxide had been separated.

The distillation was continuously carried out for 4 hours, and the results of reaction after the system had reached a steady state were as follows.

Column Top

Flow rate of distilled solution: 303 g/hr

Composition: In addition to MEA and a trace amount of carbon dioxide, 11 ppm of unknown components was observed.

Column Bottom

Flow rate of drawn solution: 137 g/hr

Composition: In addition to DEA and TEA, there were observed 280 ppm of hydroxyethyl carbamate, 6900 ppm of oxazolidone and 2600 ppm of nitrogen-containing heterocyclic compounds such as N-hydroxyethylpiperazine.

COMPARATIVE EXAMPLE 2

Distillation was continuously carried out for 4 hours by the same procedure as in Example 2 except that with regard to distillation conditions, pressure was changed to 80 torr and column bottom temperature was changed to 220° C.

The results of reaction after the system had reached a steady state were as follows.

Column Top

Flow rate of distilled solution: 303 g/hr

Composition: In addition to MEA and a trace amount of carbon dioxide, 161 ppm of unknown components was observed.

Column Bottom

Flow rate of drawn solution: 137 g/hr

Composition: In addition to DEA and TEA, there were observed 1150 ppm of hydroxyethyl carbamate, 1.3 wt. % of oxazolidone and 8200 ppm of nitrogen-containing heterocyclic compounds such as N-hydroxyethylpiperazine.

COMPARATIVE EXAMPLE 3

The collection of ammonia and carbon dioxide from the reaction solution synthesized in the reaction step of Example 1 was carried out at a column bottom solution temperature of 70° C. under reduced pressure by the use of the distillation column used in Example 1. The reaction solution was fed to this collection column at 1 kg/hr, and distillation was then carried out, with the column bottom residence time of 2 hours. As a result, carbon dioxide remained as much as 5.3% in a gas collection column bottom solution after the system had reached a steady state in accordance with the gravimetric analysis method.

COMPARATIVE EXAMPLE 4

Water and carbon dioxide were separated from a column bottom solution in Comparative Example 3. That is to say, a distillation device used in Example 1 was employed. The column bottom solution of a the gas collection column was fed at a rate of 500 g/hr and the column bottom solution was heated up to 120° C., and while a reflux ratio was maintained at 0.5, distillation was continuously carried out, with the column bottom residence time being 1 hour. As a result, 1.3% of carbon dioxide remained in the column bottom solution after the system had reached a steady state in accordance with a gravimetric analysis method.

COMPARATIVE EXAMPLE 5

The collection experiment of MEA from a column bottom solution of Comparative Example 4 was carried out by all the same procedure as in the MEA collection experiment of Example 1. The distillation was continuously carried out for 4 hours, and the results of reaction after the system had reached a steady state were as follows.

Column Top

Flow rate of distilled solution: 303 g/hr

Composition: In addition to MEA and 503 ppm (the gravimetric method) of carbon dioxide, 300 ppm of unknown components was observed.

Column Bottom

Flow rate of drawn solution: 137 g/hr

Composition: In addition to DEA and TEA, there were observed 534 ppm of hydroxyethyl carbamate, 1897 ppm of oxazolidone and 5380 ppm of nitrogen-containing heterocyclic compounds such as N-hydroxyethylpiperazine.

COMPARATIVE EXAMPLE 6

Distillation was continuously carried out for 4 hours by the same procedure as in an MEA separation step in Example 1 except that a column bottom residence time was changed into 3.2 hours. The results of reaction after the system had reached a steady state were as follows.

Column Top

Flow rate of distilled solution: 303 g/hr

Composition: In addition to MEA and a trace amount of carbon dioxide, 150 ppm of unknown components was observed.

Column Bottom

Flow rate of drawn solution: 137 g/hr

Composition: In addition to DEA and TEA, there were observed 572 ppm of hydroxyethyl carbamate, 1398 ppm of oxazolidone and 2670 ppm of nitrogen-containing heterocyclic compounds such as N-hydroxyethylpiperazine.

EXAMPLE 3

[Heat Treatment Step of Crude Alkanolamine Solution]

In an autoclave having an internal volume of 3 liters, 2.5 liters of a column bottom solution, which was a reaction solution obtained in Example 1 from which ammonia and carbon dioxide had been separated, were placed, and a heat treatment was then carried out at 185° C. for 2 hours. After the completion of the heat treatment, a treated solution was analyzed. The results are shown as follows.

Composition: Water=41.0 wt. %, MEA=41.4 wt. %, DEA=9.8 wt. %, TEA=5.8 wt. %, EG=1.22 wt. %, OXA=not detected, carbon dioxide=5142 ppm (the GC method) and 5255 ppm (the gravimetric method)

[Separation Step of Carbon Dioxide]

Next, carbon dioxide was separated from the thermally treated solution. That is to say, for distillation, there was used a packed tower (the number of theoretical plates=5 plates in a concentrating section and 5 plates in a collecting section) having an inner diameter of 40 mm and a height of 80 cm, and any reflux was not carried out. To this collection column, the thermally treated solution was fed at 1 kg/hr, and the column bottom was heated up to 190° C. on an oil bath and distillation was then carried out, with the column bottom residence time being 1 hour. In this case, the pressure in the column was 8.5 kg/cm$^2$. The results of reaction after the system had reached a steady state were as follows.

Gas Collection Column Bottom

Flow rate of solution: 450 g/hr

Composition: Water=32.5 wt. %, MEA=48.0 wt. %, DEA=11.4 wt. %, TEA=6.7 wt. %, EG=1.38 wt. %, OXA=not detected, carbon dioxide=234 ppm (the GC method) and 362 ppm (the gravimetric method)

[Separation Step of Water and Carbon Dioxide]

Next, water and carbon dioxide were separated from the column bottom solution which was the thermally treated solution from which carbon dioxide had been separated. That is to say, the column bottom solution which was the thermally treated solution from which carbon dioxide had been separated was fed at a rate of 500 g/hr to a flask of a distillation device equipped with the flask having a column bottom volume of 300 ml, a packed tower (the number of theoretical plates=10 plates in a concentrating section and 5 plates in a collecting section) having an inner diameter of 26 mm and a height of 270 cm and a reflux condenser. A pressure of 420 torr was applied and the column bottom solution was heated up to 164° C., and while the reflux ratio was maintained at 0.5, distillation was continuously carried out for 4 hours, with the column bottom residence time being 1 hour.

The results of the reaction after the system had reached a steady state were as follows.

Column Bottom

Flow rate of drawn solution: 337.5 g/hr

Composition: Water=0.26 wt. %, MEA=72.7 wt. %, DEA=17.1 wt. %, TEA=9.1 wt. %, EG=1.75 wt. %, OXA=not detected, carbon dioxide=87 ppm (the GC method) and 248 ppm (the gravimetric method)

[Separation Step of MEA]

Next, there was carried out the collection experiment of MEA from the column bottom solution from which water and carbon dioxide had been separated. That is to say, the column bottom solution from which water and carbon dioxide had been separated was fed at a rate of 500 g/hr to a distillation device used in Example 1. A pressure of 20 torr was applied and the column bottom solution was heated up to 164° C., and distillation was continuously carried out for 4 hours, with the column bottom residence time being 1.8 hours. In this case, the reflux ratio was maintained at 0.5 and the ratio of the amount of the solution distilled out through the column top to the amount of the solution drawn by side cut was maintained at 0.2.

The results of the reaction after the system had reached a steady state were as follows.

Column Top

Flow rate of distilled solution: 300 g/hr

Composition: In addition to MEA and a trace amount of carbon dioxide, 1.1 ppm of unknown components was observed.

Column Bottom

Flow rate of drawn solution: 140 g/hr

Composition: In addition to DEA and TEA, there were observed 3.3 wt. % of EG, 122 ppm of hydroxyethyl carbamate and 785 ppm of nitrogen-containing heterocyclic compounds such as N-hydroxyethylpiperazine. Any oxazolidone was not detected.

EXAMPLE 4

[Alkali Treatment Step of Crude Alkanolamine Solution]

In an autoclave having an internal volume of 3 liters, 2.5 liters of a column bottom solution, which was the reaction solution obtained in Example 1 from which ammonia and carbon dioxide had been separated, were placed and 38 g (1.5 wt. % to the solution to be treated) of calcium hydroxide was further added thereto and a heat treatment was then carried out at 175° C. for 2 hours. After the completion of the heat treatment, the thus treated solution was filtered at 80° C. to separate excessive calcium hydroxide and formed calcium carbonate. The resultant filtrate was analyzed. The results are shown as follows.

Composition: Water=41.0 wt. %, MEA=41.4 wt. %, DEA=9.8 wt. %, TEA=5.8 wt. %, EG=1.03 wt. %, OXA=not detected, carbon dioxide=140 ppm (the GC method) and 315 ppm (the gravimetric method)

[Separation Step of Water and Carbon Dioxide]

Next, water and carbon dioxide were separated from the alkali-treated filtrate. That is to say, the alkali-treated filtrate was fed at a rate of 500 g/hr to a flask of a distillation device equipped with the flask having a column bottom volume of 300 ml, a packed tower (the number of theoretical plates=10 plates in a concentrating section and 5 plates in a collecting section) having an inner diameter of 26 mm and a height of 270 cm and a reflux condenser. A pressure of 420 torr was applied and the column bottom solution was heated up to 164° C., and while the reflux ratio was maintained at 0.5, distillation was continuously carried out for 4 hours, with the column bottom residence time being 1 hour.

The results of the reaction after the system had reached a steady state were as follows.

Column Bottom

Flow rate of drawn solution: 295 g/hr

Composition: Water=0.26 wt. %, MEA=72.7 wt. %, DEA=17.1 wt. %, TEA=9.1 wt. %, EG=1.86 wt. %, OXA=not detected, carbon dioxide=70 ppm (the GC method) and 238 ppm (the gravimetric method)

[Separation Step of MEA]

Next, there was carried out the collection experiment of MEA from the column bottom solution from which water and carbon dioxide had been separated. That is to say, the column bottom solution from which water and carbon dioxide had been separated was fed at a rate of 500 g/hr to a distillation device used in Example 1. A pressure of 20 torr was applied and the column bottom solution was heated up to 164° C., and distillation was continuously carried out for 4 hours, with the column bottom residence time being 1.8 hours. In this case, the reflux ratio was maintained at 0.5 and the ratio of the amount of the solution distilled out through the column top to the amount of the solution drawn by side cut was maintained at 0.2.

The results of the reaction after the system had reached a steady state were as follows.

Column Top

Flow rate of distilled solution: 300 g/hr

Composition: In addition to MEA and a trace amount of carbon dioxide, 1 ppm of unknown components was observed.

Column Bottom

Flow rate of drawn solution: 140 g/hr

Composition: In addition to DEA and TEA, there were observed 3.1wt. % of EG, 112 ppm of hydroxyethyl carbamate and 800 ppm of nitrogen-containing heterocyclic compounds such as N-hydroxyethylpiperazine. Any oxazolidone was not detected.

What is claimed is:

1. A process for preparing alkanolamines which comprises a) a step of reacting ammonia with an alkylene oxide in the presence of a carbonate of ammonia to obtain a crude alkanolamine solution, b) a step of distilling off ammonia, carbon dioxide and water to regulate the content of carbon dioxide in the crude alkanolamine solution to 1% by weight or less, and c) a step of distilling the crude alkanolamine solution to separate and collect the alkanolamines.

2. The process for preparing alkanolamines according to claim 1 wherein the distillation of the alkanolamines is carried out under conditions such that residence time in a distillation column is 3 hours or less, thereby separating and collecting a monoalkanolamine.

3. The process for preparing alkanolamines according to claim 1 wherein the distillation of step b) is accomplished by first distilling off ammonia, carbon dioxide and a portion of the water in the crude alkanolamine solution in a distillation column bottom temperature range of from 100° to 200° C., and then distilling off additional water.

4. The process of preparing alkanolamines according to claim 1 wherein the distillation of step b) is accomplished by first distilling off ammonia, carbon dioxide and a portion of the water in the crude alkanolamine solution, and then distilling off additional water in a distillation column bottom temperature range of from 140° to 220° C.

5. The process for preparing alkanolamines according to claim 1 wherein the alkylene oxide is ethylene oxide or propylene oxide, and the alkanolamines are corresponding ethanolamines or isopropanolamines.

6. The process for preparing alkanolamines according to claim 5 wherein the distillation of ethanolamines or isopropanolamines is carried out under conditions such that the column bottom temperature of a distillation column is 200° C. or less, thereby separating and collecting a monoalkanolamine.

7. The process for preparing alkanolamines according to claim 1, wherein the distillation of the crude alkanolamine solution is carried out by separating and collecting a monoalkanolamine having a low carbon dioxide content through a column top and drawing the monoalkanolamine containing carbon dioxide in a high content by side cut to recycle the drawn solution through a step on the upstream side of a step for removing ammonia, carbon dioxide and water.

8. A process for preparing alkanolamines which comprises a) a step of reacting ammonia with an alkylene oxide in the presence of a carbonate of ammonia to obtain a crude alkanolamine solution, b) a step of subjecting the obtained crude alkanolamine solution to a heat treatment in a range of from 160° to 220° C. in the presence of water, distilling off carbon dioxide at a temperature equal to or higher than the heat treatment temperature, and then distilling off water to regulate the content of carbon dioxide in the crude alkanolamine solution to 1% by weight or less, and c) a step of distilling the crude alkanolamine solution to separate and collect the alkanolamines.

9. The process for preparing alkanolamines according to claim 8 wherein prior to the heat treatment of step b), ammonia, carbon dioxide and a portion of water are previously distilled off from the crude alkanolamine solution resulting from step a) in a distillation column bottom temperature range of from 100° to 200° C.

10. The process for preparing alkanolamines according to claim 8 wherein the removal of carbon dioxide is carried out by steam stripping.

11. The process for preparing alkanolamines according to claim 8 wherein the heat treatment is carried out, while liberated carbon dioxide is removed from the system.

12. The process for preparing alkanolamines according to claim 8 wherein water is distilled off in a distillation column bottom temperature range of from 140° to 220° C.

13. The process for preparing alkanolamines according to claim 8 wherein the alkylene oxide is ethylene oxide or propylene oxide, and the alkanolamines are corresponding ethanolamines or isopropanolamines.

14. The process for preparing alkanolamines according to claim 8, wherein the distillation of the crude alkanolamine solution is carried out by separating and collecting a monoalkanolamine having a low carbon dioxide content through a column top and drawing the monoalkanolamine containing carbon dioxide in a high content by side cut to recycle the drawn solution through a step on the upstream side of a step for removing ammonia, carbon dioxide and water.

15. A process for preparing alkanolamines which comprises a) a step of reacting ammonia with an alkylene oxide in the presence of a carbonate of ammonia to obtain a crude alkanolamine solution, b) a step of reacting the obtained crude alkanolamine solution with a base in a range of from 140° to 200° C. in the presence of water, and then distilling off water to regulate the content of carbon dioxide in the crude alkanolamine solution to 1% by weight or less, and c) a step of distilling the crude alkanolamine solution to separate and collect a monoalkanolamine.

16. The process for preparing alkanolamines according to claim 15 wherein prior to the reaction with the base, in step D) ammonia, carbon dioxide and a portion of water are previously distilled off in a distillation column bottom temperature range of from. 100° to 200° C.

17. The process for preparing alkanolamines according to claim 15 wherein after a carbonate of the base formed by reaction with the base has been removed, the distillation is carried out.

18. The process for preparing alkanolamines according to claim 15 wherein the base is a hydroxide of an alkali metal or a hydroxide of an alkaline earth metal.

19. The process for preparing alkanolamines according to claim 15 wherein water is distilled off in a distillation column bottom temperature range of from 140° to 220° C.

20. The process for preparing alkanolamines according to claim 15 wherein the alkylene oxide is ethylene oxide or propylene oxide, and the alkanolamines are corresponding ethanolamines or isopropanolamines.

21. The process for preparing alkanolamines according to claim 15, wherein the distillation of the crude alkanolamine solution is carried out by separating and collecting a monoalkanolamine having a low carbon dioxide content through a column top and drawing the monoalkanolamine containing carbon dioxide in a high content by side cut to recycle the drawn solution through a step on the upstream side of a step for removing ammonia, carbon dioxide and water.

* * * * *